United States Patent
Zochbauer et al.

(10) Patent No.: US 8,771,597 B2
(45) Date of Patent: Jul. 8, 2014

(54) APPARATUS FOR THE DETERMINATION OF A CONCENTRATION OF A COMPONENT TO BE MEASURED IN A GAS

(75) Inventors: Michael Zochbauer, Hamburg (DE); Carsten Rogge, Norderstedt (DE); Dominikus Huttner, Raisting (DE)

(73) Assignee: SICK AG, Waldkirch (DE)

( * ) Notice: Subject to any disclaimer, the term of this patent is extended or adjusted under 35 U.S.C. 154(b) by 31 days.

(21) Appl. No.: 13/471,524

(22) Filed: May 15, 2012

(65) Prior Publication Data
US 2013/0039811 A1    Feb. 14, 2013

(30) Foreign Application Priority Data
May 16, 2011  (EP) .................................. 11166178

(51) Int. Cl.
| | | |
|---|---|---|
| *G01N 21/00* | (2006.01) | |
| *G01N 30/02* | (2006.01) | |
| *G01N 17/00* | (2006.01) | |
| *G01J 3/00* | (2006.01) | |
| *G01N 30/96* | (2006.01) | |

(52) U.S. Cl.
USPC ......... 422/82.09; 422/82.05; 422/82; 422/88; 422/89; 422/91; 73/23.22; 356/51

(58) Field of Classification Search
None
See application file for complete search history.

(56) References Cited

U.S. PATENT DOCUMENTS

| | | | |
|---|---|---|---|
| 3,173,016 A | | 3/1965 | Williston et al. |
| 3,925,666 A | | 12/1975 | Allan et al. |
| 4,089,809 A | | 5/1978 | Farrior, Jr. |
| 4,115,067 A | * | 9/1978 | Lyshkow ...................... 422/425 |
| 6,497,136 B2 | * | 12/2002 | Satou ........................... 73/23.22 |
| 2001/0005981 A1 | | 7/2001 | Winchester et al. |
| 2005/0186117 A1 | * | 8/2005 | Uchiyama et al. .............. 422/91 |
| 2009/0103087 A1 | * | 4/2009 | Christian et al. .............. 356/326 |

OTHER PUBLICATIONS

"DEFOR Extractive UV Gas Analyzer", Apr. 2009, pp. 1-4, URL: http://www.baytec-inc.com/pdf/defor-extractive-analyzer.pdf. (Attached).

Imbrogno, Frank, et al., "A Comparison of Different Analytical Approaches to the On-Line Measurement of Hydrogen Sulfide", May 1996, pp. 1-20, URL: http://www.haritec.com/papers/online%20H2S.pdf. (Attached).

\* cited by examiner

*Primary Examiner* — Jill Warden
*Assistant Examiner* — Brittany Fisher
(74) *Attorney, Agent, or Firm* — Nath, Goldberg & Meyer; Jerald L. Meyer

(57) ABSTRACT

The invention relates to an apparatus for the determination of a concentration of a component to be measured in a gas, comprising a light source, a wavelength selection unit, a measurement cuvette, a reference cuvette arranged in the optical beam path in parallel thereto, at least one light receiver and an evaluation unit which determines the concentration from the signals of the light receiver, wherein the gas to be analyzed is supplied to the measurement cuvette, on the one hand, and, on the other hand, to the reference cuvette via an absorption apparatus which includes a substance which completely absorbs the component to be measured. Further, the component to be measured is $H_2S$ and a wavelength selection unit is provided for the selection of an absorption wavelength.

Figure 1:
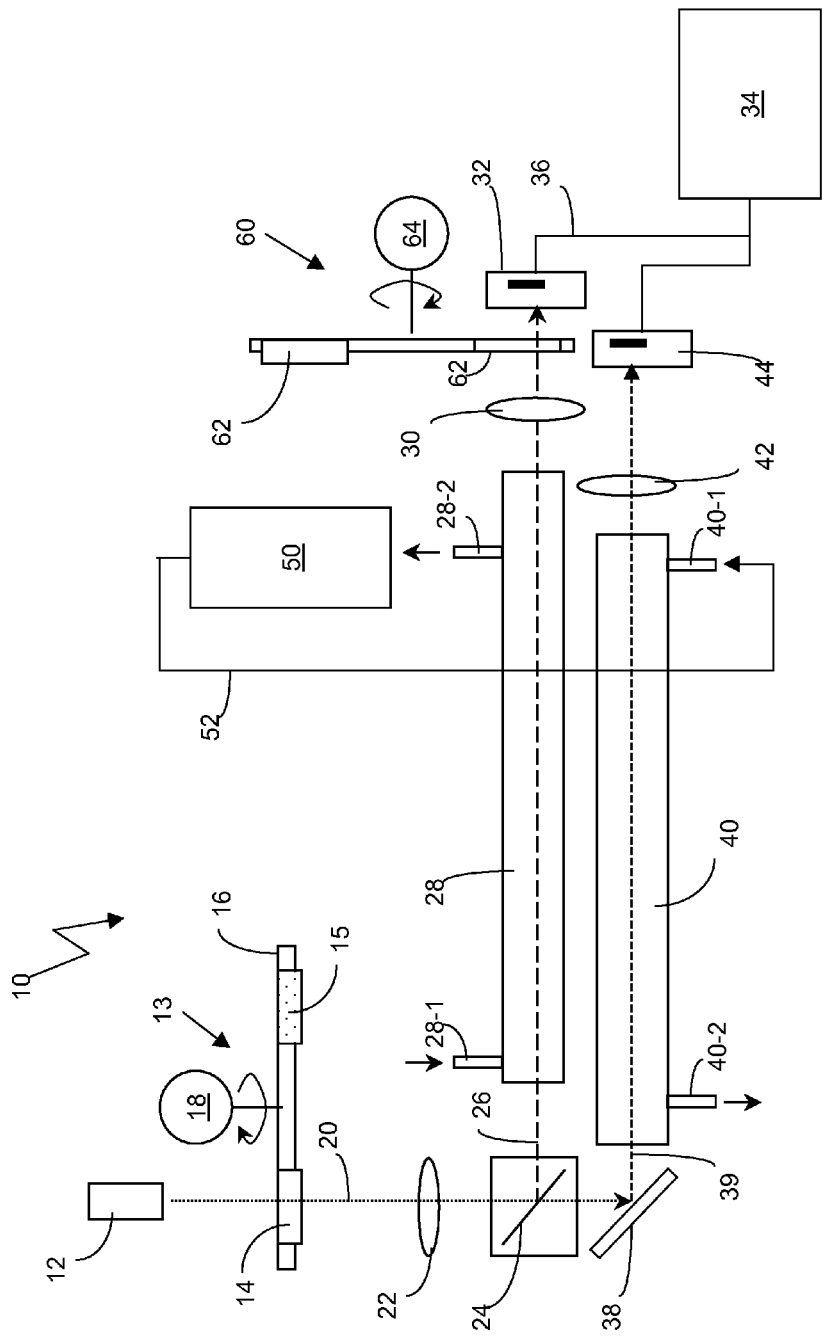

20 Claims, 3 Drawing Sheets

APPARATUS FOR THE DETERMINATION OF A CONCENTRATION OF A COMPONENT TO BE MEASURED IN A GAS

The invention relates to an apparatus for the determination of a concentration of a component to be measured, in particular $H_2S$, in a gas comprising a light source, a measurement cuvette, a reference cuvette arranged in the optical beam path in parallel thereto, at least one light receiver and an evaluation unit which determines the concentration from the signals of the light receiver.

Traditionally, paper tape processes are used for the selective $H_2S$ measurement which use a selective chemical reaction between $H_2S$ and, for example, lead acetate. It is a disadvantage thereof that paper tape methods only work quasi continuously, are very demanding and, in particular intensive in maintenance. A paper roll soaked with lead acetate only keeps for two to four weeks on average.

Furthermore, UV simultaneous spectrometers are known by means of which a higher selectivity can be achieved by chemometric methods. Simultaneous spectrometers are, however, very demanding from a technical point of view. It is furthermore disadvantageous that only a limited selectivity is achievable for $H_2S$ when the gas matrix includes further sulfur components, in particular mercaptanes. The $H_2S$ spectrum only marginarilly differs from the mercaptan spectra.

Finally, simple UV photometers are available which work on the principle of the interference filter correlation method. One of these is known supplied by the applicants under the mark DEFOR. However, these have the disadvantage that on the measurement of $H_2S$ very high transverse sensitivities are present with respect to other sulfur compounds, for example, $SO_2$, $COS$, $CS_2$ and, in particular mercaptan. These can hardly be reduced by spectroscopic means or by transverse sensitivity corrections.

From U.S. Pat. No. 3,173,016 an apparatus in accordance with the preamble of claim 1 is known for the measurement of the mercury content in air.

Starting from this state of the art it is the object of the invention to provide an apparatus which has an improved selectivity, in particular for $H_2S$, for less demand in time, effort and cost.

This object is satisfied by an apparatus for the determination of a concentration of a component to be measured in a gas comprises,
 a light source,
 a measurement cuvette,
 a reference cuvette arranged in the optical beam path in parallel thereto,
 at least one light receiver,
 an evaluation unit that determines the concentration from the signals of the light receiver, with
the gas to be analyzed being supplied to the measurement cuvette, on the one hand, and, on the other hand, via an absorption apparatus which includes a substance which completely absorbs the component to be measured to the reference cuvette. In accordance with the invention, the component to be measured is $H_2S$ and a wavelength selection unit is provided for the selection of the absorption wavelength.

A neutral gas is not taken as a reference now, in contrast to known photometers, but rather the gas to be analyzed itself is used, however, reduced by the component to be measured. In this respect, the measurement gas initially flows unchanged through the measurement cuvette. The light receiver, which receives the measurement light thus "sees" the sum of the actual measurement effect (i.e. the absorption by the measurement component $H_2S$) and all transverse sensitivities.

The absorption apparatus is introduced into the supply to the reference cuvette which now selectively removes the component to be measured ($H_2S$), but lets the remaining components pass through unchanged. The gas thereby reduced by the component to be measured then flows through the reference cuvette. The light receiver which receives the reference light, then only "sees" the transverse sensitivities without the actual measurement effect. The concentration of the component to be measured results from the difference between measurement light and reference light.

The particular advantage lies, on the one hand, in the use of a simple photometer and, on the other hand, in the very high selectivity which is ultimately achieved by means of the absorber. As a whole a cost-effective possibility is thereby created to determine the gas content of $H_2S$ in a highly selective manner.

The object is further satisfied by a corresponding method which is also described herein and having the steps:
 guiding of the gas to be analyzed through a measurement cuvette,
 guiding of the gas through an absorption apparatus and removal of the component to be measured from the gas;
 further guiding of the gas from the absorption apparatus to a reference cuvette and through this to an outlet;
 generation of a light beam of an absorption wavelength ($\lambda_{Abs}$) in which the component shows an absorption;
 guiding of the light beam through the measurement cuvette for the receipt of measurement light and parallel thereto through the reference cuvette for the receipt of reference light;
 generation of received signals by means of separate receipt of measurement light and of reference light;
 determination of the concentration from the received signals.

In principle, the components to be measured can be determined by means of a simple difference formation, as mentioned above. However, in order to achieve a high long term stability and to measure drift-free it is provided in an embodiment of the invention that a respective light receiver is supplied both for the light passing through the measurement cuvette and also for the light passing through the reference cuvette and measurements are carried for two different wavelengths—one at which the component to be measured is absorbed and one at which it is not absorbed—and then the concentration is determined in the evaluation unit by means of the double formation of quotients.

In a first embodiment of the apparatus the gas to be analyzed flows serially initially through the measurement cuvette, then through the absorption apparatus and finally through the reference cuvette. Such a serial setup with respect to the gas guidance is relatively simple and correspondingly cost-conscious.

In order to match the timely response at the measurement and the reference path as good as possible, the gas to be analyzed is guided in parallel through the measurement and reference path in a second embodiment. In this respect the gas is supplied to the measurement cuvette, on the one hand, and, on the other hand, is supplied to the reference cuvette via the absorption apparatus. However, in order to now match the timely response, a current matching apparatus is additionally arranged in the supply to the measurement cuvette which, from a construction point of view, is of identical design to the first absorption apparatus, but does not include any substance absorbing the component to be measured. Therefore, equal flow conditions are present both in the measurement passage and also in the reference passage which positively affects the timely response.

In an embodiment of the invention the absorption apparatus is configured as a cartridge flowed through by the gas, in which an absorber is arranged which includes the absorbing substance. Advantageously, the loading of the absorber with $H_2S$ is optically detectable, in particular in terms of color, so that it is directly apparent when the absorber is to be exchanged.

Elements of the fifth main group have been found to be particularly selective as $H_2S$ absorbing substances.

These are preferably present in combination with halides, for example, $SbCl_3$, $SbBr_3$, $SbCl_5$ for the avoidance of $SO_2$ absorption.

In an embodiment the absorbing substance includes a two-component buffer system having an acid with 0<pKs<2 as a first component and a hydroxide salt as a second component. A buffer acid with this pKs value avoids, on the one hand, a reaction with $SO_2$ and, on the other hand, it effects that the reaction with $H_2S$ runs completely. For example, trichloro acetic acid or dichloro acetic acid come into consideration as a buffer acid and, for example, NaOH, KOH, $Mg(OH)_2$, $Al(OH)_3$ as a hydroxide salt.

In order to slow down the drying out of the absorber, the absorbing substance includes a hygroscopic halide compound, for example $MgCl_2$ or $AlCl_3$.

This watery absorber solution is stored in a suitable carrier material, preferably silica gel. By means of storage at the solid material it is possible to realize a solid absorber which advantageously lets itself be constructed in the shape of an absorption cartridge.

Such an absorber can be operated at normal temperatures of approximately 0° up to approximately 100°.

Figure 2:
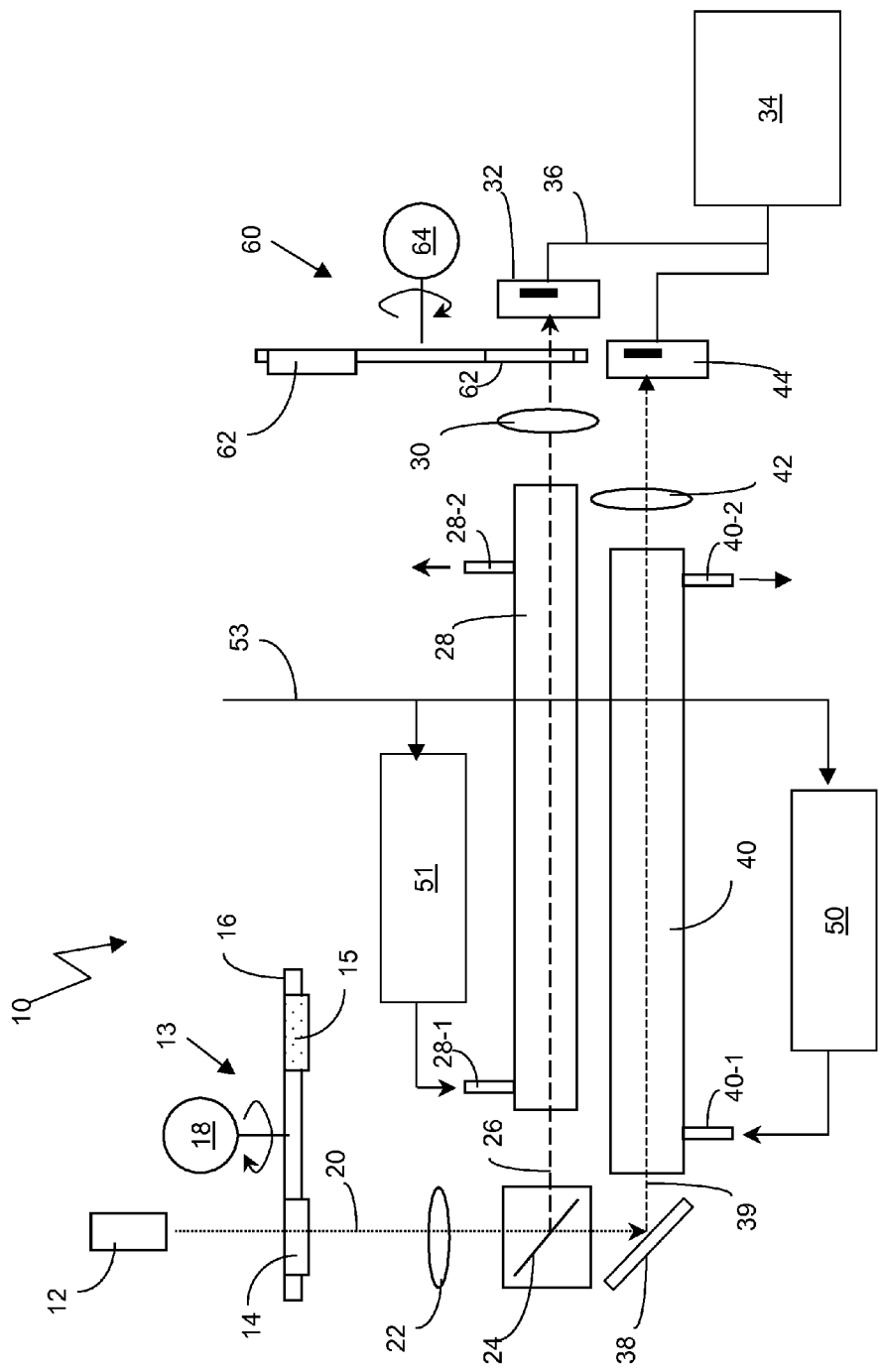
Figure 4:
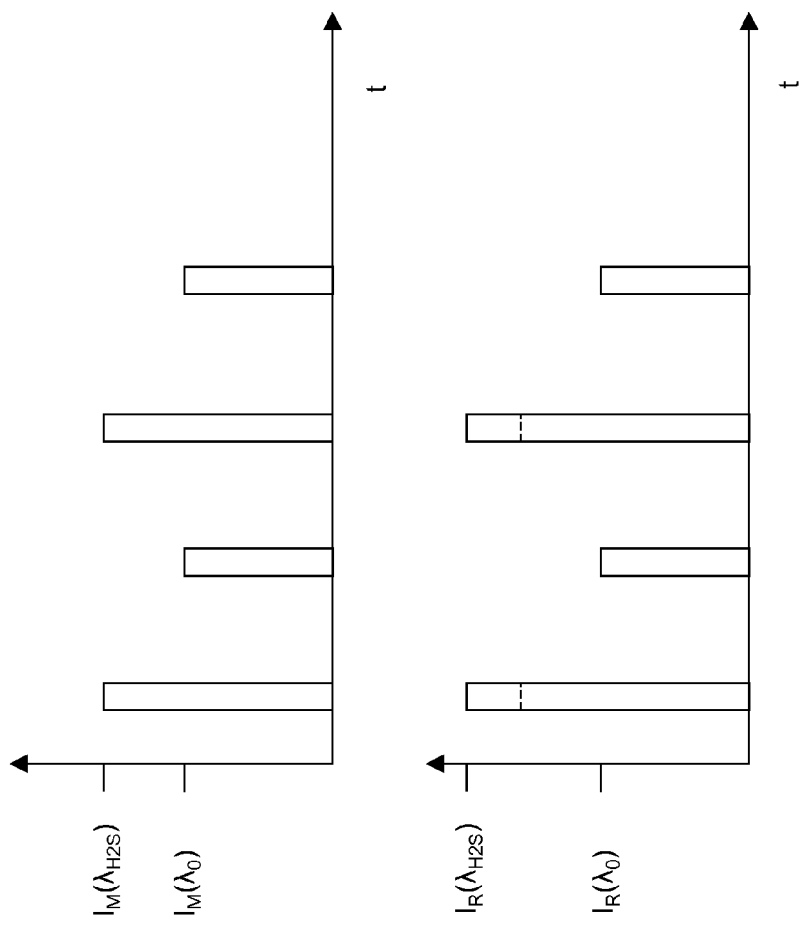
Figure 3:
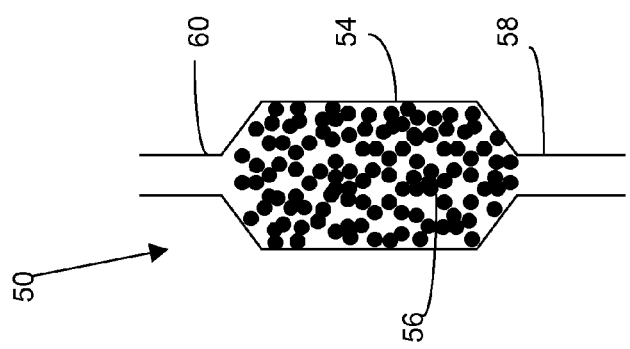

In the following the invention will be described by means of an embodiment with reference to the drawing in detail. In the drawing there is shown:

FIG. 1 a schematic setup of an apparatus in accordance with the invention;

FIG. 2 a further embodiment of the apparatus with parallel gas supply;

FIG. 3 a schematic illustration of an absorption apparatus;

FIG. 4 a schematic illustration of the received light intensity.

An apparatus 10 in accordance with the invention is constructed in the manner of a photometer and has a light source 12, in particular a UV light source. This light source 12 emits light of different wavelengths which is why a wavelength selection unit 13 is provided for the selection of a certain desired wavelength. The wavelength selection unit 13 includes optical filters 14, 15 which can be pivoted into the optical path via a filter wheel 16. The filter wheel 16 is driven via a step motor 18.

The transmitted light which is referred to in the drawing by means of the reference numeral 20 is bundled by the optic 22 and is incident on a semipermeable splitting mirror 24.

A first part of the light beam 20, which is illustrated in FIG. 1 as a dotted line and has the reference numeral 26, passes a measurement cuvette 28 and following the passage through the measurement cuvette 28 is guided to a measurement detector 32 via an optic 30. The detector 32 transforms the received light into an electric signal corresponding to the intensity which is passed onto an evaluation unit 34 via a line 36.

A second part 39 of the light beam 20 which was divided by the splitter mirror 24 is guided through a reference cuvette 40 via a total mirror 38 and is finally supplied to a reference detector 44 via a receiving optics 42 which, already like the measurement detector 32 transforms the light into electric signals and supplies the signals to the evaluation unit 34.

In a first embodiment (FIG. 1), the measurement gas which should be analyzed, i.e. whose content of a desired component to be measured should be determined, is supplied to a measurement cuvette inlet 28-1 from where it flows through the measurement cuvette 28 and is led away again via a measurement cuvette outlet 28-2. The gas is supplied to an absorption apparatus 50 from the measurement cuvette outlet 28-2 in which an absorber 56 having an absorbing substance is provided which completely absorbs the component to be measured. The absorption apparatus 50 having the absorber 56 will be explained below in more detail with reference to FIG. 3. From the absorption apparatus 50 the gas, which now no longer includes the component to be measured, is supplied to a reference cuvette inlet 40-1 via a line 52 and then passes through the reference cuvette 40 up to a reference cuvette outlet 40-2 via which the gas finally exits from the reference cuvette 40. The gas is thus serially guided through the measurement cuvette 28, the absorption apparatus 50 and the reference cuvette 40 in this embodiment.

In a second embodiment (FIG. 2) the gas is guided in parallel through the measurement cuvette 28 and the reference cuvette 40. For this purpose the gas is supplied in parallel to the absorption apparatus 50 and a current matching apparatus 51 via a line 53. From the current matching apparatus 51 the gas is then guided to the measurement cuvette 28, i.e. the measurement cuvette inlet 28-1. In the other branch the gas is supplied from the absorption apparatus 50 to the reference cuvette, i.e. to the reference cuvette inlet 40-1. The two parallel branches thus consist, on the one hand, of the current matching apparatus 51 and the measurement cuvette 28 (measurement branch) and, on the other hand, of the absorption apparatus 50 and the reference cuvette 40 (reference branch). In this respect, the current matching apparatus 51 is of identical design to the absorption apparatus 50 from a construction point of view; however, the current matching apparatus 51 does not include any absorbing substance. It therefore only serves for the matching of the gas current conditions.

The apparatus 10 is suitable for measuring $H_2S$ as a component to be measured of a gas. This means that $H_2S$ should be completely absorbed in the absorption apparatus 50. For this purpose the absorption apparatus 50 is designed as follows (FIG. 3):

The absorption apparatus 50 has a cartridge-like body 54 in which the actually absorbing substance is arranged. In FIG. 3 the absorber comprising a carrier material and absorbing substance is referred to by means of the reference numeral 56. The cartridge 54 is designed such that the gas, which enters at the one end face 58 and exits again at the other end face 60, flows through the overall absorber 56 as much as possible.

Starting point of the absorbing substance are materials of the fifth main group which selectively absorb the $H_2S$, such as for example, As, Sb, Bi. In order to avoid $SO_2$ absorptions, halides are selected in combination with these materials, such as for example, $SbCl_3$, $SbBr_3$ or $SbCl_5$. In order to avoid a reaction of the absorber with $SO_2$ a buffer acid with a pKs value of <2 must be selected and in order to completely process the $H_2S$ action the pKs value should be >0. Therefore a pH value of between 0 and 2 is set. The buffer system itself only consists of a first component, namely an acid with 0<pKs<2, for example, trichloro acetic acid or dichloro acetic acid and a second component in the form of a hydroxide salt, such as for example, NaOH, KOH, $Mg(OH)_2$ or $Al(OH)_3$. Through a partial neutralization of the first component with the second component a buffer system with a pH value of between 0 and 2 arises. Furthermore, one or more strongly hydroscopic halide compounds are added to the absorber in order to slow down the drying out of the absorber. Such a halide compound can be, for example $MgCl_2$ or $AlCl_3$ or such like. The so prepared watery absorber solution is stored in a suitable carrier material. In an advantageous manner this carrier material is a silica gel having a corn size of several millimeters. It is possible to realize a solid absorber 56 which can be constructed well in the form of a cartridge 54 through the storage of the watery absorber solution in the silica gel. This absorber 56 also has the properties that on loading with $H_2S$ it discolors so that on the discoloration of the contents of the cartridge 54 one can determine when the absorbing substance has been completely used up. Then the overall absorber 56 has namely completely discolored from the absorber entrance 58 up to the outlet 60.

In the following it will now be explained how the concentration of the component to be measured is determined.

In a first very simple embodiment of the method the basic principle becomes evident. Initially one of the filters 14 is brought into the light beam so that the light beam 20 includes a desired wavelength at which the component to be measured (here $H_2S$) shows an absorption. This wavelength shall be termed absorption wavelength in the following.

The first part 26 of the light beam 20 passes through the measurement cuvette 28 in which the light is at least partially absorbed and indeed by the components of the measurement gas, and, in particular also by the component to be measured. The thus weakened light beam 26 is then incident at the detector 32 and is registered there with an intensity $I_M(\lambda_{Abs})$. Thus $I_M(\lambda_{Abs})$ describes the intensity at the measurement detector at an absorption wavelength $\lambda_{Abs}$.

In the parallel branch the second part 39 of the light passes through the reference cuvette 40. Since the reference cuvette includes the same gas, but reduced by the component to be measured, the same absorptions are present there with the exception of the absorption by the component to be measured. For this reason a higher intensity $I_R(\lambda_{Abs})$ is measured at the reference detector 44 at the absorption wavelength.

The difference between these two intensities $I_M(\lambda_{Abs})-I_R(\lambda Abs)$ therefore corresponds to the absorption by the component to be measured in the measurement cuvette 28, so that the evaluation unit 34 can determine the concentration of a component to be measured therefrom.

This correlation is also indicated in FIG. 4. The change in intensity which corresponds to the absorption by the component to be measured is illustrated as the portion of $I_R(\lambda_{Abs})$ which lies above the dotted line.

However, in order to obtain a good long term stability and to be as independent as possible from possible drifts, for example, due to temperatures or aging appearances it is provided in a further embodiment of the method in accordance with the invention to not carry out the intensity measurement at the absorption wavelength, but rather also at a non-absorption wavelength $\lambda_0$, i.e. at a wavelength at which the component to be measured is not absorbed. The non-absorption wavelength $\lambda_0$ is thereby generated in that a corresponding filter 15 of the filter wheel 16 is pivoted into the optical path. The corresponding intensities which are then measured at the measurement detector 32 and that the reference detector 44 are referred to as $I_M(\lambda_0)$ and $I_R(\lambda_0)$ (see also FIG. 4) and are determined just for the intensities at the absorption wavelength. Then the concentration of the component to be measured can be determined in a manner known per se from the double formation of quotients, so that in this respect changes due to drifts, aging appearances and such like can be compensated, for the most part.

$$\frac{\frac{I_M(\lambda_0)}{I_R(\lambda_0)} - \frac{I_M(\lambda_{Abs})}{I_R(\lambda_{Abs})}}{\frac{I_M(\lambda_0)}{I_R(\lambda_0)}}$$

For calibration and alignment purposes an alignment unit 60 can be provided which comprises the test cuvette 62 which can be pivoted into the optical path by means of a motor 64 for calibration and alignment purposes, so that a calibration to known sizes can be carried out.

The invention claimed is:

1. An apparatus for the determination of a concentration of a component to be measured in a gas, comprising:
   a light source (12);
   a measurement cuvette (28) including an input opening and outlet opening, positioned to receive light from the light source;
   an absorption apparatus having an inlet and an outlet, positioned in fluid communication with the measurement cuvette via the outlet opening of the measurement cuvette;
   a reference cuvette (40) having an input opening and an outlet opening, arranged in the optical beam path in parallel to the measurement cuvette, the outlet of the absorption apparatus in fluid communication with the input end of the reference cuvette;
   at least one light receiver (32, 44);
   and an evaluation unit (34) which determines the concentration from the signals of the light receiver (32, 44),
   wherein the gas to be analyzed is supplied to the measurement cuvette (28), on the one hand, and, on the other hand, via an absorption apparatus (50) which includes a substance which completely absorbs the component to be measured to the reference cuvette (40),
   wherein the component to be measured is $H_2S$ and wherein a wavelength selection unit (13) is provided for the selection of an absorption wavelength ($\lambda_{Abs}$), and
   wherein the gas to be analyzed flows serially, initially through the measurement cuvette (28) arranged to receive gas and discharge gas into the absorption apparatus (50), then through the absorption apparatus (50) arranged to receive gas and discharge gas into the reference cuvette (40), and is finally guided through the reference cuvette (40) arranged to receive gas and discharge gas.

2. An apparatus in accordance with claim 1, wherein the absorption apparatus (50) is configured as a cartridge (54) arranged to receive gas and discharge gas, wherein the cartridge contains an absorber (56) which includes the absorbing substance.

3. An apparatus in accordance with claim 2, wherein the absorber (56) includes silica gel as a carrier for the absorbing substance.

4. An apparatus in accordance with claim 3, wherein the absorbing substance comprises elements of the fifth main group.

5. An apparatus in accordance with claim 4, wherein the elements of the fifth main group are present in combination with halides.

6. An apparatus in accordance with claim 4, wherein the absorbing substance includes a two-component buffer system having an acid with $0<pKs<2$ as a first component and a hydroxide salt as a second component.

7. An apparatus in accordance with claim 4, wherein the absorbing substance includes a hygroscopic halide compound.

8. An apparatus in accordance with claim 2, wherein the loading of the absorber (56) with $H_2S$ is optically detectable.

9. An apparatus in accordance with claim 8, wherein the loading of the absorber with $H_2S$ is optically detectable in terms of color.

10. An apparatus in accordance with claim 1, wherein a respective light receiver is arranged to receive and transform light into an electric signal and pass to the evaluation unit (34), both for the light (26) passing through the measurement cuvette (28) and for the light (39) passing through the reference cuvette (40) and the evaluation unit (34) is configured to determine the concentration by means of the double formation of quotients.

11. An apparatus for the determination of a concentration of a component to be measured in a gas, comprising:
- a light source (12);
- a measurement cuvette (28) including an input opening and outlet opening, positioned to receive light from the light source;
- an absorption apparatus having an inlet and an outlet, positioned in fluid communication with the measurement cuvette via the outlet opening of the measurement cuvette;
- a reference cuvette (40) having an input opening and an outlet opening, arranged in the optical beam path in parallel to the measurement cuvette the outlet of the absorption apparatus in fluid communication with the input end of the reference cuvette;
- at least one light receiver (32, 44);
- and an evaluation unit (34) which determines the concentration from the signals of the light receiver (32, 44),
- wherein the gas to be analyzed is supplied to the measurement cuvette (28), on the one hand, and, on the other hand, via an absorption apparatus (50) which includes a substance which completely absorbs the component to be measured to the reference cuvette (40),
- wherein the component to be measured is $H_2S$ and wherein a wavelength selection unit (13) is provided for the selection of an absorption wavelength ($\lambda_{Abs}$), and
- wherein the gas to be analyzed is supplied in parallel to the measurement cuvette (38) arranged to receive gas and discharge gas into the absorption apparatus, on the one hand, and, on the other hand, via the absorption apparatus (50) arranged to receive and discharge gas into the reference cuvette (40), wherein a current matching apparatus (51) is arranged in the supply for the measurement cuvette (28) which, from a construction point of view, is of identical design to the first absorption apparatus (50), but does not include any substance absorbing the component to be measured.

12. An apparatus in accordance with claim 11, wherein the absorption apparatus (50) is configured as a cartridge (54) arranged to receive gas and discharge gas, wherein the cartridge contains an absorber (56) which includes the absorbing substance.

13. An apparatus in accordance with claim 12, wherein the absorber (56) includes silica gel as a carrier for the absorbing substance.

14. An apparatus in accordance with claim 13, wherein the absorbing substance comprises elements of the fifth main group.

15. An apparatus in accordance with claim 14, wherein the elements of the fifth main group are present in combination with halides.

16. An apparatus in accordance with claim 14, wherein the absorbing substance includes a two-component buffer system having an acid with $0<pKs<2$ as a first component and a hydroxide salt as a second component.

17. An apparatus in accordance with claim 14, wherein the absorbing substance includes a hygroscopic halide compound.

18. An apparatus in accordance with claim 12, wherein the loading of the absorber (56) with $H_2S$ is optically detectable.

19. An apparatus in accordance with claim 18, wherein the loading of the absorber with $H_2S$ is optically detectable in terms of color.

20. An apparatus in accordance with claim 11, wherein a respective light receiver is arranged to receive and transform light into an electric signal and pass to the evaluation unit (34), both for the light (26) passing through the measurement cuvette (28) and for the light (39) passing through the reference cuvette (40) and the evaluation unit (34) is configured to determine the concentration by means of the double formation of quotients.

* * * * *